(12) United States Patent  
Kerr

(10) Patent No.: US 9,375,260 B2
(45) Date of Patent: Jun. 28, 2016

(54) SURGICAL INSTRUMENT WITH NON-CONTACT ELECTRICAL COUPLING

(71) Applicant: COVIDIEN LP, Mansfield, MA (US)

(72) Inventor: Duane E. Kerr, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 310 days.

(21) Appl. No.: 14/080,581

(22) Filed: Nov. 14, 2013

(65) Prior Publication Data

US 2014/0074085 A1 Mar. 13, 2014

Related U.S. Application Data

(62) Division of application No. 12/758,524, filed on Apr. 12, 2010, now Pat. No. 8,597,295.

(51) Int. Cl.
 *A61B 18/14* (2006.01)
(52) U.S. Cl.
 CPC ......... *A61B 18/1445* (2013.01); *A61B 18/1402* (2013.01); *A61B 2018/1455* (2013.01)
(58) Field of Classification Search
 CPC ............. A61B 18/085; A61B 18/1442; A61B 18/1445; A61B 18/1447; A61B 2018/1455; A61B 2018/00589; A61B 2018/00595
 See application file for complete search history.

(56) References Cited

U.S. PATENT DOCUMENTS

| | | | |
|---|---|---|---|
| D249,549 S | 9/1978 | Pike | |
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D343,453 S | 1/1994 | Noda | |
| D348,930 S | 7/1994 | Olson | |
| D349,341 S | 8/1994 | Lichtman et al. | |
| 5,334,215 A | 8/1994 | Chen | |
| D354,564 S | 1/1995 | Medema | |
| 5,395,033 A | 3/1995 | Byrne et al. | |
| D358,887 S | 5/1995 | Feinberg | |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

U.S. Appl. No. 08/926,869, filed Sep. 10, 1997, James G. Chandler.

(Continued)

*Primary Examiner* — Michael Peffley

(57) ABSTRACT

A surgical instrument includes a reusable base component including a handle and an electrically activatable modular component removably coupled to the base component. The modular component includes an end effector operable from the handle to treat tissue. The end effector is responsive to manipulation of the handle. A first energy storage component is disposed onboard the base component and is electrically coupled to a source of electricity. A second energy storage component is disposed onboard the modular component and is electrically insulated from the first energy storage component. The second energy storage component is arranged such that a current may be selectively induced in the modular component by delivery of electrical energy to the first energy storage component.

6 Claims, 5 Drawing Sheets

(56) References Cited

U.S. PATENT DOCUMENTS

| | | |
|---|---|---|
| 5,437,277 A | 8/1995 | Dumoulin et al. |
| 5,467,911 A | 11/1995 | Tsuruta et al. |
| 5,575,805 A | 11/1996 | Li |
| 5,582,617 A | 12/1996 | Klieman et al. |
| 5,611,798 A | 3/1997 | Eggers |
| D384,413 S | 9/1997 | Zlock et al. |
| 5,665,100 A | 9/1997 | Yoon |
| 5,720,744 A | 2/1998 | Eggleston et al. |
| H1745 H | 8/1998 | Paraschac |
| 5,792,165 A | 8/1998 | Klieman et al. |
| D402,028 S | 12/1998 | Grimm et al. |
| 5,849,020 A | 12/1998 | Long et al. |
| D408,018 S | 4/1999 | McNaughton |
| 5,916,215 A | 6/1999 | Long et al. |
| 5,951,549 A | 9/1999 | Richardson et al. |
| 5,951,552 A | 9/1999 | Long et al. |
| D416,089 S | 11/1999 | Barton et al. |
| 6,053,933 A | 4/2000 | Balazs et al. |
| D424,694 S | 5/2000 | Tetzlaff et al. |
| D425,201 S | 5/2000 | Tetzlaff et al. |
| 6,106,519 A * | 8/2000 | Long .................. A61B 18/1487 604/164.01 |
| H1904 H | 10/2000 | Yates et al. |
| 6,187,002 B1 | 2/2001 | Long et al. |
| 6,206,875 B1 | 3/2001 | Long et al. |
| 6,270,508 B1 | 8/2001 | Klieman et al. |
| 6,277,117 B1 | 8/2001 | Tetzlaff et al. |
| D449,886 S | 10/2001 | Tetzlaff et al. |
| 6,306,131 B1 | 10/2001 | Hareyama et al. |
| D453,923 S | 2/2002 | Olson |
| D454,951 S | 3/2002 | Bon |
| 6,371,967 B1 * | 4/2002 | Long .................. A61B 18/1487 606/167 |
| D457,958 S | 5/2002 | Dycus et al. |
| D457,959 S | 5/2002 | Tetzlaff et al. |
| 6,409,728 B1 | 6/2002 | Ehr et al. |
| H2037 H | 7/2002 | Yates et al. |
| D465,281 S | 11/2002 | Lang |
| D466,209 S | 11/2002 | Bon |
| 6,676,660 B2 | 1/2004 | Wampler et al. |
| D493,888 S | 8/2004 | Reschke |
| D496,997 S | 10/2004 | Dycus et al. |
| D499,181 S | 11/2004 | Dycus et al. |
| 6,840,938 B1 | 1/2005 | Morley et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,491,201 B2 | 2/2009 | Shields et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 8,112,871 B2 | 2/2012 | Brandt et al. |
| 8,133,254 B2 | 3/2012 | Dumbauld et al. |
| 8,162,965 B2 | 4/2012 | Reschke et al. |
| 8,187,273 B2 | 5/2012 | Kerr et al. |
| D661,394 S | 6/2012 | Romero et al. |
| 8,266,783 B2 | 9/2012 | Brandt et al. |
| 8,277,446 B2 | 10/2012 | Heard |
| 8,287,536 B2 | 10/2012 | Mueller et al. |
| 8,292,067 B2 | 10/2012 | Chowaniec et al. |
| 8,292,886 B2 | 10/2012 | Kerr et al. |
| 8,323,310 B2 | 12/2012 | Kingsley |
| 8,343,150 B2 | 1/2013 | Artale |
| 8,343,151 B2 | 1/2013 | Siebrecht et al. |
| 8,357,159 B2 | 1/2013 | Romero |
| 8,388,647 B2 | 3/2013 | Nau, Jr. et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,876 B2 | 4/2013 | Kappus et al. |
| 8,430,877 B2 | 4/2013 | Kerr et al. |
| 8,439,911 B2 | 5/2013 | Mueller |
| 8,439,913 B2 | 5/2013 | Horner et al. |
| 8,597,295 B2 | 12/2013 | Kerr |
| 2003/0139742 A1 | 7/2003 | Wampler et al. |
| 2008/0039836 A1 | 2/2008 | Odom et al. |
| 2010/0042101 A1 | 2/2010 | Inagaki et al. |
| 2010/0204697 A1 | 8/2010 | Dumbauld et al. |
| 2010/0204698 A1 | 8/2010 | Chapman et al. |
| 2010/0217258 A1 | 8/2010 | Floume et al. |
| 2010/0280511 A1 | 11/2010 | Rachlin et al. |
| 2011/0034918 A1 | 2/2011 | Reschke |
| 2011/0046623 A1 | 2/2011 | Reschke |
| 2011/0054468 A1 | 3/2011 | Dycus |
| 2011/0054471 A1 | 3/2011 | Gerhardt et al. |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0073594 A1 | 3/2011 | Bonn |
| 2011/0077648 A1 | 3/2011 | Lee et al. |
| 2011/0082494 A1 | 4/2011 | Kerr et al. |
| 2011/0118736 A1 | 5/2011 | Harper et al. |
| 2011/0184405 A1 | 7/2011 | Mueller |
| 2011/0190653 A1 | 8/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0251605 A1 | 10/2011 | Hoarau et al. |
| 2011/0251606 A1 | 10/2011 | Kerr |
| 2011/0251611 A1 | 10/2011 | Horner et al. |
| 2011/0270250 A1 | 11/2011 | Horner et al. |
| 2011/0270251 A1 | 11/2011 | Horner et al. |
| 2011/0276048 A1 | 11/2011 | Kerr et al. |
| 2011/0276049 A1 | 11/2011 | Gerhardt |
| 2011/0295251 A1 | 12/2011 | Garrison |
| 2011/0295313 A1 | 12/2011 | Kerr |
| 2011/0301599 A1 | 12/2011 | Roy et al. |
| 2011/0301600 A1 | 12/2011 | Garrison et al. |
| 2011/0301602 A1 | 12/2011 | Roy et al. |
| 2011/0301603 A1 | 12/2011 | Kerr et al. |
| 2011/0301604 A1 | 12/2011 | Horner et al. |
| 2011/0301605 A1 | 12/2011 | Horner |
| 2011/0301606 A1 | 12/2011 | Kerr |
| 2011/0319886 A1 | 12/2011 | Chojin et al. |
| 2011/0319888 A1 | 12/2011 | Mueller et al. |
| 2012/0010614 A1 | 1/2012 | Couture |
| 2013/0325043 A1 | 12/2013 | Butcher |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |

(56) References Cited

FOREIGN PATENT DOCUMENTS

| | | |
|---|---|---|
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 | 12/2001 |
| DE | 20121161 | 4/2002 |
| DE | 10045375 C2 | 10/2002 |
| DE | 20 2007 009318 | 8/2007 |
| DE | 202007009317 U1 | 8/2007 |
| DE | 20 2007 009165 | 10/2007 |
| DE | 20 2007 01623 | 3/2008 |
| DE | 19738457 B4 | 1/2009 |
| DE | 102004026179 B4 | 1/2009 |
| DE | 10 2008 018406 | 7/2009 |
| EP | 1 159 926 A2 | 12/2001 |
| EP | 0888747 B1 | 12/2004 |
| EP | 1281878 | 10/2005 |
| EP | 2153791 | 2/2010 |
| JP | 61-501068 | 9/1984 |
| JP | 65-502328 | 3/1992 |
| JP | 5-5106 | 1/1993 |
| JP | 05-40112 | 2/1993 |
| JP | 6-030945 | 2/1994 |
| JP | 6-121797 | 5/1994 |
| JP | 6-285078 | 10/1994 |
| JP | 6-511401 | 12/1994 |
| JP | 06343644 A | 12/1994 |
| JP | 07265328 A | 10/1995 |
| JP | 8-317936 | 3/1996 |
| JP | 08056955 A | 3/1996 |
| JP | 8-289895 | 5/1996 |
| JP | 08252263 A | 10/1996 |
| JP | 8-317934 | 12/1996 |
| JP | 9-000538 | 1/1997 |
| JP | 09010223 A | 1/1997 |
| JP | 9-122138 | 5/1997 |
| JP | 10-000195 | 1/1998 |
| JP | 10-24051 | 1/1998 |
| JP | 10-155798 | 6/1998 |
| JP | 11-47149 | 2/1999 |
| JP | 11-47150 | 2/1999 |
| JP | 11-070124 A | 3/1999 |
| JP | 11-169381 | 6/1999 |
| JP | 11-192238 | 7/1999 |
| JP | 11244298 A | 9/1999 |
| JP | 2000-102545 A | 4/2000 |
| JP | 2000-135222 | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001128990 A | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2005-312807 | 10/2005 |
| JP | 2006-015078 | 1/2006 |
| JP | 2006/501939 | 1/2006 |
| JP | 2006-095316 | 4/2006 |
| JP | 2011/125195 | 6/2011 |
| SU | 401367 A1 | 10/1973 |
| WO | 95/20921 | 8/1995 |
| WO | 0036986 A1 | 6/2000 |
| WO | WO 00/59392 | 10/2000 |
| WO | WO 01/15614 | 3/2001 |
| WO | 0154604 A1 | 8/2001 |
| WO | WO 02/45589 | 6/2002 |
| WO | 2005/110264 A2 | 11/2005 |
| WO | WO 2006/021269 | 3/2006 |
| WO | WO 2008040483 | 4/2008 |
| WO | WO 2011/018154 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/833,823, filed Mar. 15, 2013, Garrison.
U.S. Appl. No. 13/838,945, filed Mar. 15, 2013, Stoddard.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 14/017,572, filed Sep. 4, 2013, Arya.
U.S. Appl. No. 14/019,031, filed Sep. 5, 2013, Garrison.
U.S. Appl. No. 14/019,094, filed Sep. 5, 2013, Garrison.
U.S. Appl. No. 14/032,486, filed Sep. 20, 2013 Kendrick.
U.S. Appl. No. 14/035,423, filed Sep. 24, 2013, Garrison.
U.S. Appl. No. 14/037,772, filed Sep. 26, 2013, Frushour.
U.S. Appl. No. 14/041,995, filed Sep. 30, 2013, Kendrick.
U.S. Appl. No. 14/042,947, filed Oct. 1, 2013, Craig.
U.S. Appl. No. 14/043,039, filed Oct. 1, 2013, Rusin.
U.S. Appl. No. 14/043,322, filed Oct. 1, 2013, O'Neill.
U.S. Appl. No. 14/047,474, filed Oct. 7, 2013, Mueller.
U.S. Appl. No. 14/050,593, filed Oct. 10, 2013, Plaven.
U.S. Appl. No. 14/052,827, filed Oct. 14, 2013, Nau.
U.S. Appl. No. 14/052,856, filed Oct. 14, 2013, Latimer.
U.S. Appl. No. 14/052,871, filed Oct. 14, 2013, Kappus.
U.S. Appl. No. 14/054,173, filed Oct. 15, 2013, Payne.
U.S. Appl. No. 14/054,573, filed Oct. 15, 2013, Harper.
U.S. Appl. No. 14/064,310, filed Oct. 28, 2013, Reschke.
U.S. Appl. No. 14/064,702, filed Oct. 28, 2013, Townsend.
U.S. Appl. No. 14/065,644, filed Oct. 29, 2013, Reschke.
U.S. Appl. No. 14/080,564, filed Nov. 14, 2013, Lawes.
U.S. Appl. No. 14/080,581, filed Nov. 14, 2013, Kerr.
U.S. Appl. No. 14/083,696, filed Nov. 19, 2013, Homer.
U.S. Appl. No. 14/086,399, filed Nov. 21, 2013, Allen.
U.S. Appl. No. 14/091,505, filed Nov. 27, 2013, Garrison.
U.S. Appl. No. 14/091,521, filed Nov. 27, 2013, Garrison.
U.S. Appl. No. 14/091,532, filed Nov. 27, 2013, Garrison.
U.S. Appl. No. 14/098,953, filed Dec. 6, 2013, Cunningham.
U.S. Appl. No. 14/100,237, filed Dec. 9, 2013, Reschke.
U.S. Appl. No. 14/103,971, filed Dec. 12, 2013, Roy.
U.S. Appl. No. 14/105,374, filed Dec. 13, 2013, Moua.
U.S. Appl. No. 14/109,459, filed Dec. 17, 2013, Hoarau.
U.S. Appl. No. 14/149,343, filed Jan. 7, 2014, Schmaltz.
U.S. Appl. No. 14/152,618, filed Jan. 10, 2014, Artale.
U.S. Appl. No. 14/152,690, filed Jan. 10, 2014, Hart.
U.S. Appl. No. 14/153,346, filed Jan. 13, 2014, Collings.
U.S. Appl. No. 14/162,192, filed Jan. 23, 2014, Garrison.
Japanese Office Action dated Aug. 7, 2014 issued in Japanese Application No. 2011-87649.
European Search Report No. 1116118 dated Oct. 12, 2011.
European Search Report for European Application No. 11179514.2 dated Nov. 4, 2011.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hennorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium,

(56) References Cited

OTHER PUBLICATIONS and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'L Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.

(56) References Cited

OTHER PUBLICATIONS

Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Japanese Office Action dated Feb. 26, 2015 issued in JP Application No. 201187649.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.

* cited by examiner

SURGICAL INSTRUMENT WITH NON-CONTACT ELECTRICAL COUPLING

CROSS-REFERENCE TO RELATED APPLICATIONS

This application is a divisional of U.S. patent application Ser. No. 12/758,524, filed Apr. 12, 2010, now U.S. Pat. No. 8,597,295. the contents of which is hereby incorporated by reference in its entirety.

BACKGROUND

1. Technical Field

The present disclosure relates generally the field of reusable surgical instruments. In particular, the disclosure relates electrical couplings for instruments having separable and replaceable components to provide clean, sterile or refurbished surfaces in each instance of use.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode surface to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis. Thereafter, the sealed tissue may be transected by advancing a knife through the jaws. A detailed discussion of the use of an electrosurgical forceps may be found in U.S. Pat. No. 7,255,697 to Dycus et al.

In use, various tissue-contacting components of an electrosurgical forceps tend to become contaminated or degraded. For example, electrodes may become contaminated as portions of the treated tissue adhere to the tissue-contacting surfaces of the electrodes. Also, a knife blade may become dull and less effective in transecting sealed tissue after repeated use, even in a single surgical procedure. In order to provide clean electrodes and a sharp knife for a particular surgical procedure, a brand new instrument is often used. Once the procedure is complete, the used instrument is discarded.

Instruments that are reusable for multiple procedures reduce the instrumentation costs per procedure. Some reusable forceps include a reusable component adapted for persistent use coupled to a removable and replaceable component adapted for limited use. The reusable component may include, for example, a control element such as a handle that remains primarily outside the surgical field. The handle may be constructed ruggedly to sustain regular and recurring usage in numerous surgical procedures. The removable and replaceable component may include a tool element, such as an end effector containing the delicate and tissue-contacting wear surfaces. Replacing a worn end effector to refurbish an instrument provides refreshed surfaces with minimal waste.

Providing replaceable components for a reusable electrosurgical forceps, however, presents various challenges. For example, many of these instruments require arduous disassembly and reassembly procedures to ensure proper electrical continuity is provided between the reusable and replaceable components. Also, electrical couplings on the reusable component may be difficult to clean.

SUMMARY

The present disclosure describes a surgical instrument for treating tissue. The instrument includes a reusable base component with a handle assembly and an electrically-activated modular component removably coupled to the base component. The modular component includes an end effector operable from the handle assembly to treat tissue, and the end effector is responsive to manipulation of the handle assembly to move between first and second configurations. A first energy storage component is disposed onboard the base component, and the first energy storage component is electrically coupled to a source of electricity. A second energy storage component is disposed onboard the modular component. The second energy storage component is electrically insulated from the first energy storage component and is arranged with respect to the first energy storage component such that a current may be selectively induced in the modular component by delivery of electrical energy to the first energy storage component.

The first energy storage component may include a first inductive coil and the second energy storage component may include a second inductive coil. The second inductive coil may be inductively coupled to the first inductive coil such that a current is induced in the second coil in response to a current flow in the first coil.

The source of electricity may be an electrosurgical generator, and the modular component may include at least one electrode. The electrode may be electrically coupled to the second coil and configured for delivering electrosurgical energy to tissue.

The modular component may include pair of opposing jaw members, and one or both of the jaw member may be movable between an open configuration wherein the jaw members are substantially spaced for receiving tissue and a closed configuration wherein the jaw members are closer together for clamping tissue therebetween. The end effector may include a sensor for detecting a parameter of the tissue treatment, and the sensor may be powered by the induced current in the second coil. The sensor may be a gap sensor configured to detect a separation distance between the opposing jaw members.

The first energy storage component may include a first capacitor having a pair of conductive plates separated by a dielectric material. The second energy storage component may include a second capacitor having a pair of conductive plates arranged on opposite sides of the first capacitor. Each of the conductive plates of the second capacitor may be separated from a conductive plate of the first capacitor by a dielectric material. The conductive plates of the second capacitor may be arranged on a respective opposing jaw member.

According to another aspect of the disclosure, a modular end effector for a surgical instrument includes an electrically-activated component and an inductor coil electrically coupled to the electrically-activated component. The end effector includes a contactless mechanical interface configured to removably couple the end effector to a corresponding interface on a base component of the surgical instrument. The mechanical interface is electrically isolated from the electrically-activated component.

The end effector may include a pair of opposing jaw members, and one or both of the jaw members may be movable between an open configuration wherein the jaw members are substantially spaced for receiving tissue and a closed configuration wherein the jaw members are closer together for clamping tissue therebetween. The electrically-activated component may include an electrode disposed on an opposed clamping surface of one of the jaw members, and the contactless mechanical interface may include a linkage for receiving reciprocal motion from the base component. The linkage may be operable to move the at least one of the pair of jaw members between the open configuration and the closed configuration.

According to another aspect of the disclosure, a surgical instrument includes a reusable base component with a handle assembly and an elongated tube extending distally from the handle assembly. An electrically-activated modular component is removably coupled to the base component, and the modular component includes a pair of jaw members operable from the handle assembly and configured to move between an open configuration wherein the jaw members are substantially spaced for receiving tissue and a closed configuration wherein the jaw members are closer together for clamping tissue. A first capacitor plate is operatively associated with the elongated tube, and a second capacitor plate is operatively associated with one of the jaw members. The second capacitor plate forms a capacitor with the first capacitor plate to capacitively couple the base component and the modular component.

The first capacitor plate may be electrically coupled to a source of electrosurgical energy, the second capacitor plate may be electrically coupled to an electrode configured to deliver the electrosurgical energy to tissue. A pair of capacitor plates may be operatively associated with the elongated tube, and each of the jaw members may include a capacitor plate forming a respective capacitor with a respective capacitor plate of the elongated tube.

The one of the jaw members may include a pair of capacitor plates straddling the first capacitor plate on the elongated tube. The pair of capacitor plates of the one of the jaw members may define legs of a generally U-shaped conductive portion of the first jaw member.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
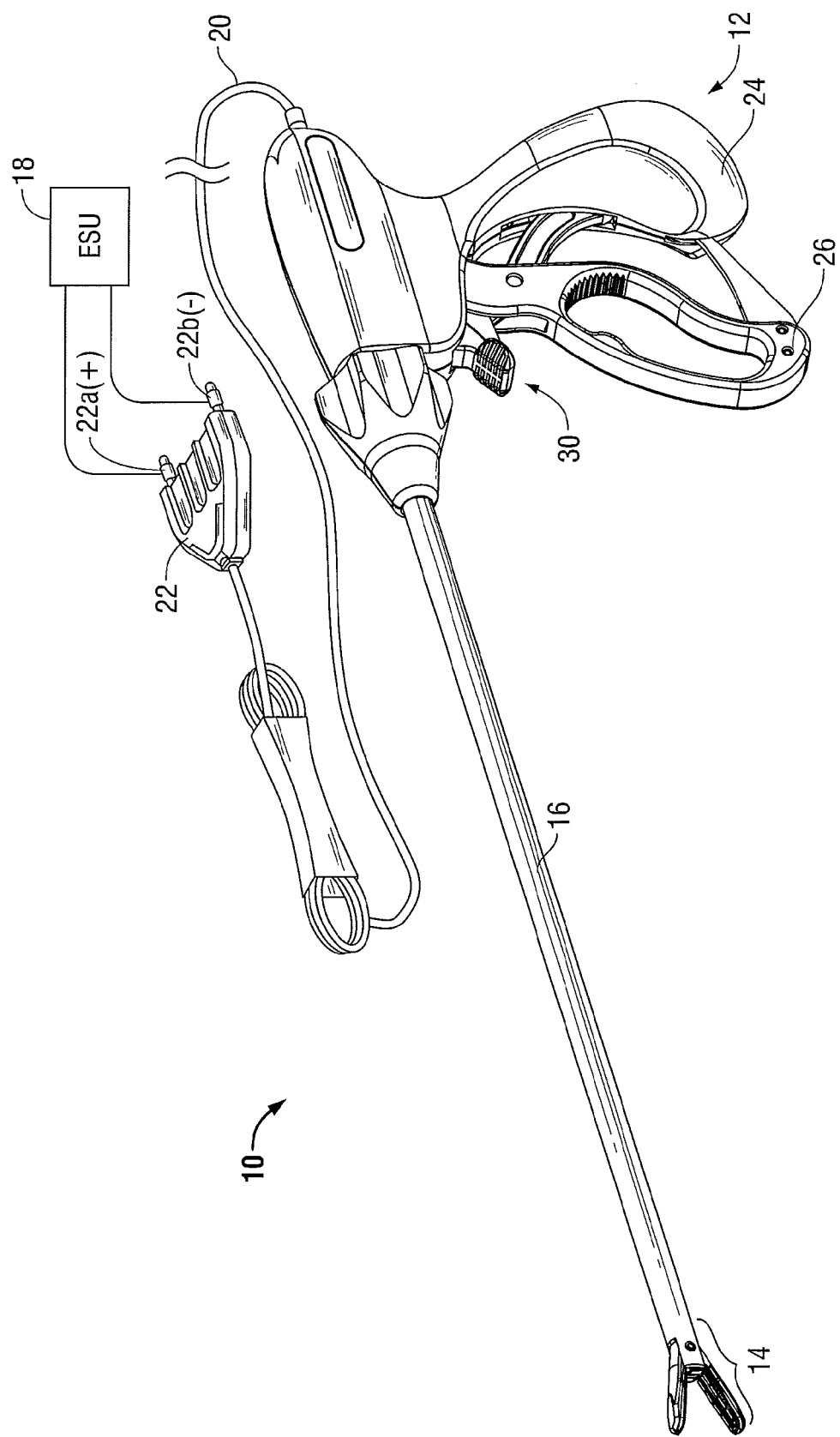
FIG. 1 is a perspective view of an endoscopic surgical instrument in accordance with an embodiment of the present disclosure having modular jaw members inductively coupled to a distal end of an elongated shaft.

Referring initially to FIG. 1, an embodiment of an electrosurgical instrument 10 is depicted. The instrument 10 includes a handle assembly 12, an end effector 14 and an elongated shaft 16 therebetween. A surgeon may manipulate the handle assembly 12 to remotely control the end effector 14 through the elongated shaft 16. This configuration is typically associated with instruments for use in laparoscopic or endoscopic surgical procedures. Various aspects of the present disclosure may also be practiced with traditional open instruments (see FIG. 5), and in connection with endoluminal procedures as well.

The instrument 10 is coupled to a source of electrosurgical energy, e.g., an electrosurgical generator 18. The generator 18 may include devices such as the LIGASURE™ Vessel Sealing Generator and the Force Triad™ Generator as sold by Covidien. A cable 20 extends between the handle assembly 12 and the generator 18, and includes a connector 22 for coupling the instrument 10 to the generator 18. The connector 22 includes two prong members 22a and 22b that are dimensioned to mechanically and electrically connect the instrument 10 to opposite terminals, e.g., positive or active (+) and negative or return (−) terminals associated with the generator 18. Thus, bipolar energy may be provided through the instrument 10. Alternatively, the instrument 10 may be configured for delivering monopolar energy to the tissue. In a monopolar configuration, the instrument 10 delivers electrosurgical energy from an active terminal, e.g. (+), while a return pad (not shown) is placed generally beneath a patient and provides a return path to the opposite terminal, e.g. (−), of the generator 18.

To control the end effector 14, the handle assembly 12 includes a stationary handle 24 and movable handle 26. The movable handle 26 may be separated and approximated relative to the stationary handle 24 to respectively open and close the end effector 14. A trigger 30 is also disposed on the handle assembly 12, and is operable to extend and retract a knife 76 (FIG. 3) through the end effector 14. A footswitch (not shown) may be provided to initiate and terminate the delivery of electrosurgical energy to the end effector 14.

Figure 2:
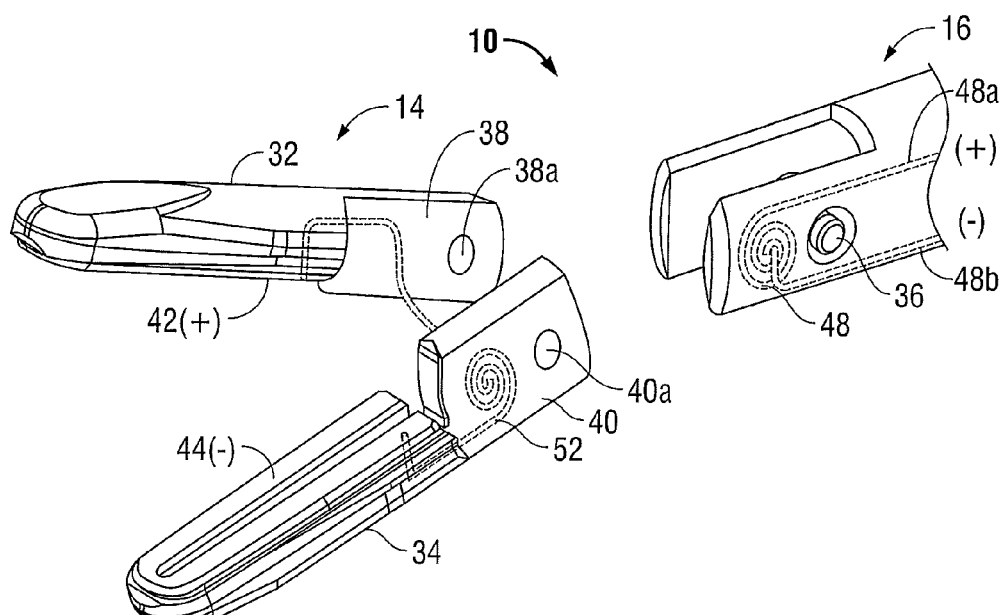
FIG. 2 is an enlarged, perspective view of a distal end of the instrument of FIG. 1 depicting the modular jaw members separated from the elongated shaft.

Referring now to FIG. 2, end effector 14 includes upper and lower jaw members 32 and 34. Each of the modular jaw members 32, 34 is coupled to the elongated shaft 16 about a pivot pin 36. The jaw members 32, 34 include respective proximal flanges 38, 40 extending into a bifurcated distal end of the elongated shaft 16, where a respective bore 38a, 40a engages the pivot pin 36. The proximal flanges 38, 40 are operatively associated with the movable handle 26 (FIG. 1) to open and close the jaw members 32, 34. The jaw members 32, 34 are movable between an open configuration where the jaw members 32, 34 are substantially spaced to receive tissue and a closed configuration where the jaw members 32, 34 are closer together to clamp the tissue therebetween. Retraction of the movable handle 26 induces the jaw members 32, 34 to move to the open configuration and separation of the movable handle 26 from the stationary handle 24 induces the jaw members 32, 34 to move to the closed configuration.

Various mechanisms may be provided to operatively associate the movable handle 26 with the proximal flanges 38, 40. For example, the movable handle 26 may be coupled to a reciprocating member (not shown) that extends through the elongated shaft 16 as described in commonly owned U.S. Pat. No. 7,255,697 to Dycus et al. The reciprocating member may engage cam slots (not shown) on each of the proximal flanges 38, 40 to change the position of both of the jaw members 32, 34 relative to the elongated shaft. This type of construction induces bilateral jaw motion. Other unilateral constructions are also envisioned in which only one jaw member 32, 34 moves with respect to the elongated shaft.

When clamped about tissue, the jaw members 32, 34 may deliver electrosurgical energy to the tissue through a pair of opposed electrodes 42, 44. The electrodes 42, 44 are configured to selectively apply an effective amount of pressure and electrosurgical energy to the tissue. The opposed electrodes are associated with opposite electrical potentials (+), (−) to permit an electrosurgical current to flow through the tissue situated between the jaw members 32, 34 to effect a tissue seal.

The modular jaw members 32 and 34 are selectively removable from the elongated shaft 16 to facilitate replacement the jaw members 32, 34 following a surgical procedure. Replacement of the jaw members 32, 34 may serve to refurbish the instrument 10 for subsequent use. The pivot pin 36 may be spring loaded to retain the flanges 38 and 40 within the bifurcated distal end of the elongated shaft 16 when the instrument 10 is in use. Following an electrosurgical procedure, the spring loaded pivot pin 36 may be manipulated to release the used jaw members 32, 34 without requiring a cumbersome disassembly process. Thereafter, the pivot pin 36 may snap into a set of bores 38a, 40a of a clean, new or refurbished set of jaw members 32, 34.

In the illustrated embodiment, when the jaw members 32, 34 are connected to the elongated shaft, a contactless electrical coupling is established. The proximal flange 40 of lower jaw member 34 is inductively coupled to the elongated shaft 16 through a pair of spiral coils 48, 52. The spiral coils 48, 52 form inductors, which store energy by generating a magnetic field when an electrical current is passed therethrough. The first coil 48 is disposed onboard the elongated shaft 16, which forms part of a reusable base component of the instrument 10. The first coil 48 is electrically coupled to the two prongs 22a, 22b of the connector 22 (FIG. 1) through respective lead wires 48a, 48b extending through the instrument 10. The two lead wires 48a, 48b may be associated with the opposite electrical potentials of the prongs 22a (+), 22b (−). The second coil 52 is disposed on board the modular jaw member 34, which forms a replaceable component of the instrument 10. The second coil 52 is electrically coupled to the two electrodes 42 (+) and 44 (−) of opposite electrical potential.

The coils 48, 52 are constructed of an appropriate electrically conductive material, such as copper or stainless steel wire. The coils 48, 52 are separated by an electrically insulative material such that no direct contact exists between the coils 48, 52. One or both of the elongated shaft 16 and the proximal flange 40 of the lower jaw member 34 may be constructed of an insulative material such as a ceramic or reinforced plastic that contains the respective coil 48, 52. The insulative material protects the coils 48, 52 from mechanical damage, and may form a flat interface on the exterior of the respective component 16, 40 that may be cleaned without undue difficulty.

The coils 48, 52 are arranged such that when the lower jaw member 34 is installed, the coils 48, 52 are axially aligned, and face-to-face in parallel planes. The two coils 48, 52 are spatially as close to one another as is practical since inductive coupling is most effective at short distances. In use, a current is supplied by the electrosurgical generator 18 (FIG. 1) to the first coil 48. The current in the first coil 48 generates a magnetic field passing through the second coil 52. The magnetic field induces a current in the second coil 52 that is used to power the electrodes 42, 44.

Figure 3:
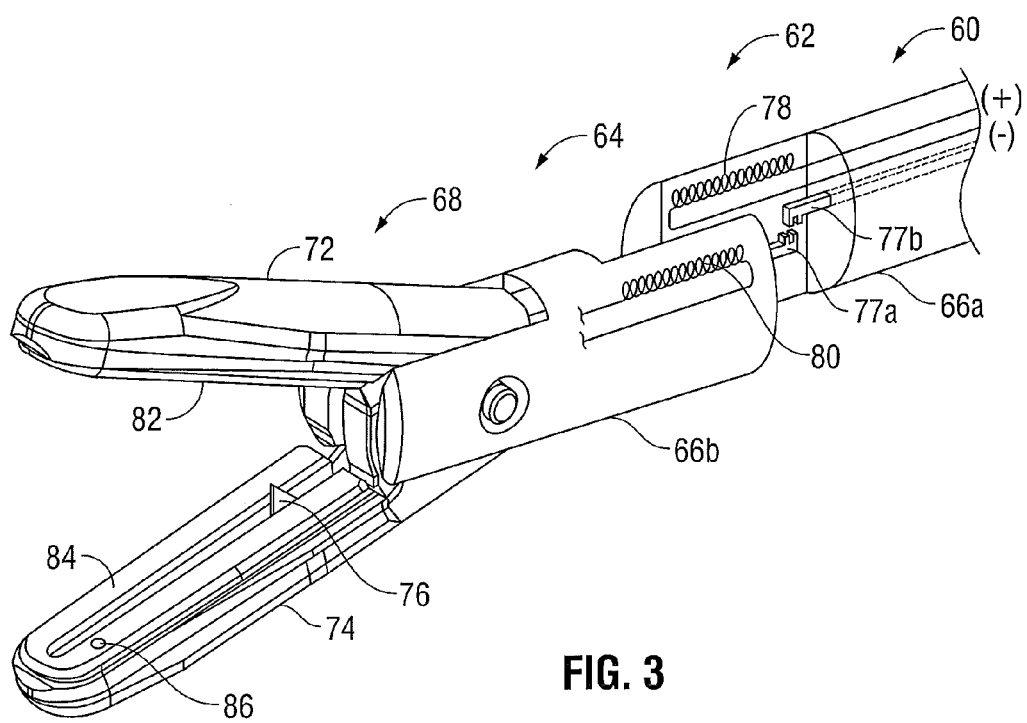
FIG. 3 is a perspective view of an alternate embodiment of an instrument in accordance with the present disclosure having a modular end effector separated from an elongated shaft.

Referring now to FIG. 3, an alternate embodiment of an instrument 60 includes a reusable base component 62 and a removable modular component 64. The base component 62 includes a first elongated shaft portion 66a extending from a handle assembly 12 (see FIG. 1), and the modular component 64 includes a second elongated shaft component 66b extending to an end effector 68. The two elongated shaft portions 66a, 66b may be mechanically fastened to one another to permit mechanical motion of jaw members 72, 74 between open and closed configurations and advancement and retraction of an optional reciprocating knife blade 76 through the lower jaw member 74.

Advancement of the reciprocating knife 76 permits the transaction of tissue, particularly once the tissue has been sealed. To facilitate the mechanical motion of the jaw members 72, 74 and/or the knife blade 76, the modular component 64 includes a first linkage 77a for receiving reciprocal motion from a corresponding second linkage 77b on the base component 62. The first linkage 77a may be directly coupled to the knife 76 such that reciprocal motion of the first linkage 77a induces a corresponding reciprocal motion in the knife 76. Alternatively or additionally, the reciprocal motion of the first linkage may be converted to pivotal motion of the jaw members 72, 74 through the use of cam surfaces (not shown) or other conventional mechanisms. The second linkage 77b extends to the handle assembly 12 (FIG. 1) and may receive reciprocal motion therefrom.

An electrical coupling between the modular component 64 and the base component 62 may be established by inductive coupling. The base component 62 includes a first coil 78 electrically coupled to the opposite poles of electrosurgical generator 18 (FIG. 1). The modular component includes a second coil 80 that may be coupled to electrodes 82 and 84. First and second coils 78, 80 are longitudinally arranged in respective elongated shaft portions 66a, 66b. The elongated shaft portions 66a, 66b provide ample length for a significant number of coils. The coils 78, 80 are laterally separated from one another. Other configurations are envisioned, such as a coaxial configuration wherein one coil is situated longitudinally within the other. This type of electrical coupling permits a contactless mechanical interface to be established between the removable component 64 and the base component 62. The mechanical interface may be contactless in that electricity is not transmitted through any of the mechanically engaging surfaces such that the mechanical interface is electrically isolated from the electrodes 82, 84.

In addition to the electrodes 82, 84, other electrical devices may be included on the modular component 64 to be powered by a current flowing through the second coil 80. For example, a gap sensor 86 is included on the lower jaw member 74. The gap sensor 86 is configured to sense the separation or "gap distance" between the jaw members 72, 74. An appropriate gap distance for generating an effective tissue seal may be between about 0.001 inches and about 0.006 inches. A gap distance between about 0.002 inches and about 0.003 inches may be preferred in some instances. The gap sensor 86 may include any suitable sensor such as optical sensor, and may receive power and communicate data with the electrosurgical generator 18 through the inductive coupling. An appropriate gap sensor is described in commonly owned U.S. Patent Application Publication No. 2009/0204114 to Odom.

Figure 4A:
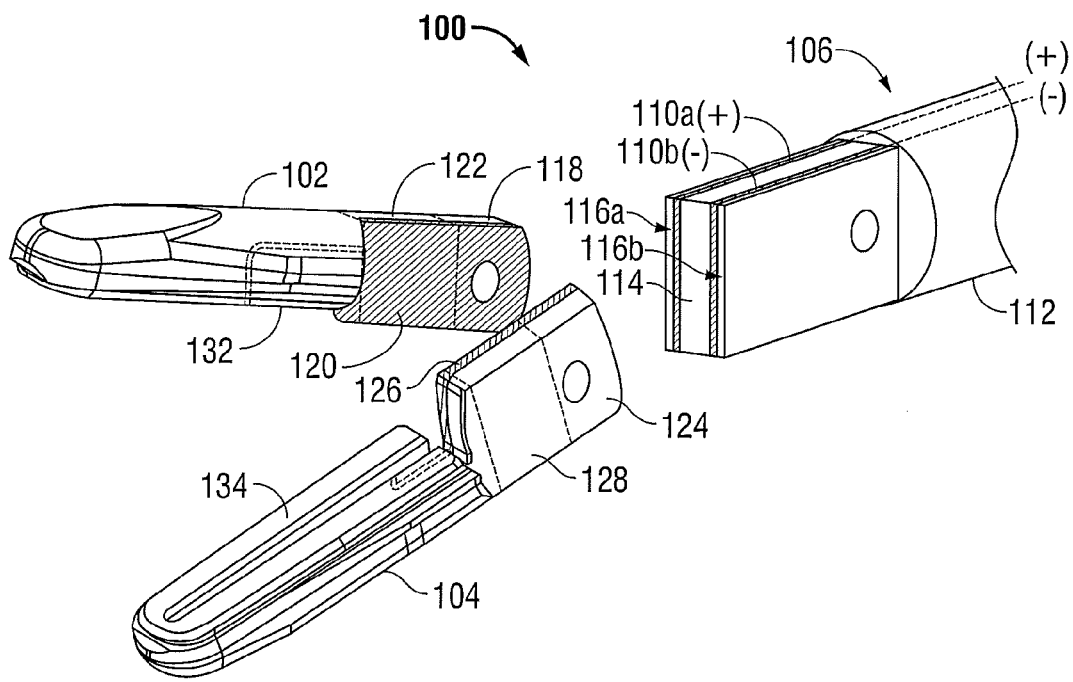
FIG. 4A is a perspective view of an alternate embodiment of an instrument in accordance with the present disclosure having modular jaw members for capacitive coupling with an elongated shaft.

Referring now to FIG. 4A, an alternate embodiment of an instrument 100 includes modular jaw members 102, 104 configured for non-contact, capacitive coupling with a base component 106. The base component 106 includes a pair of electrically conductive plates 110a, 110b disposed at a distal end of an elongated shaft 112. The plates 110a, 110b are coupled to the electrosurgical generator 18 (FIG. 1) such that a first conductive plate 110a is coupled to a first terminal of the generator, e.g. active (+), and a second conductive plate 110b is coupled to a second terminal, e.g. return (−). The conductive plates 110a, 110b are separated by an electrically insulative, dielectric material 114. A pair of dielectric plates 116a and 116b are disposed laterally exterior to the conductive plates 110a, 110b.

A proximal flange 118 of the upper jaw member 102 includes a flat-plate electrically conductive portion 120 adjacent a structural body portion 122. Similarly, a proximal flange 124 of the lower jaw member 104 includes a flat-plate electrically conductive portion 126 adjacent a structural body portion 128. The conductive plate portions 120, 126 are in electrical communication with respective electrodes 132, 134.

Figure 4B:
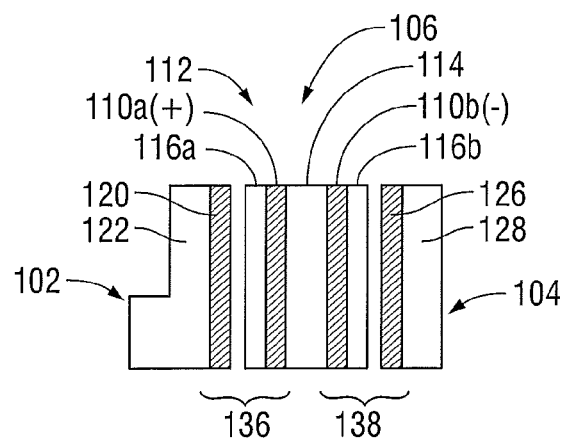
FIG. 4B is a cross-sectional view of the modular jaw members of FIG. 4A capacitively coupled to the elongated shaft.

The modular jaw members 102, 104 may be assembled to the base component 106 as depicted in FIG. 4B. The distal end of elongated shaft 112 is interposed between the electrically conductive plates 120, 126 of the jaw members 102, 104. The dielectric plate 116a is interposed between conductive plates 110a and 120 to define a first parallel plate capacitor 136. The conductive plate 120 of the upper jaw member 102 may thus be capacitively coupled to the base component 106. The dielectric plate 116b is similarly interposed between conductive plates 110b and 126 to define a second capacitor 138. The conductive plate 126 of the lower jaw member 104 may thus be capacitively coupled to the base component 106.

Figure 4C:
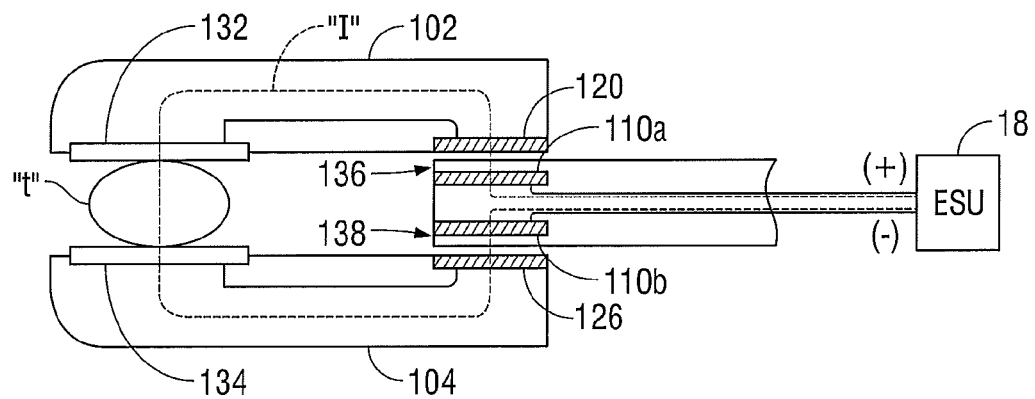
FIG. 4C is a schematic view of a current path through tissue captured between the modular jaw members of FIG. 4A.

When the modular jaw members 102, 104 are assembled to the base component 106 and tissue "t" is captured between the electrodes 132, 134, an electrosurgical current "I" may be induced through the tissue "t" as indicated in FIG. 4C. Electrosurgical energy, such as electrosurgical current "I" at a predetermined output frequency and power may pass from a first terminal, e.g. an active terminal (+), of the generator 18 through the first capacitor 136 to upper jaw member 102. The current "I" is transmitted through the active electrode 132 and the tissue "t" to return electrode 134. The current "I" returns through second capacitor 138 to a second terminal, e.g., a return terminal (−), of the generator 18.

Figure 5:
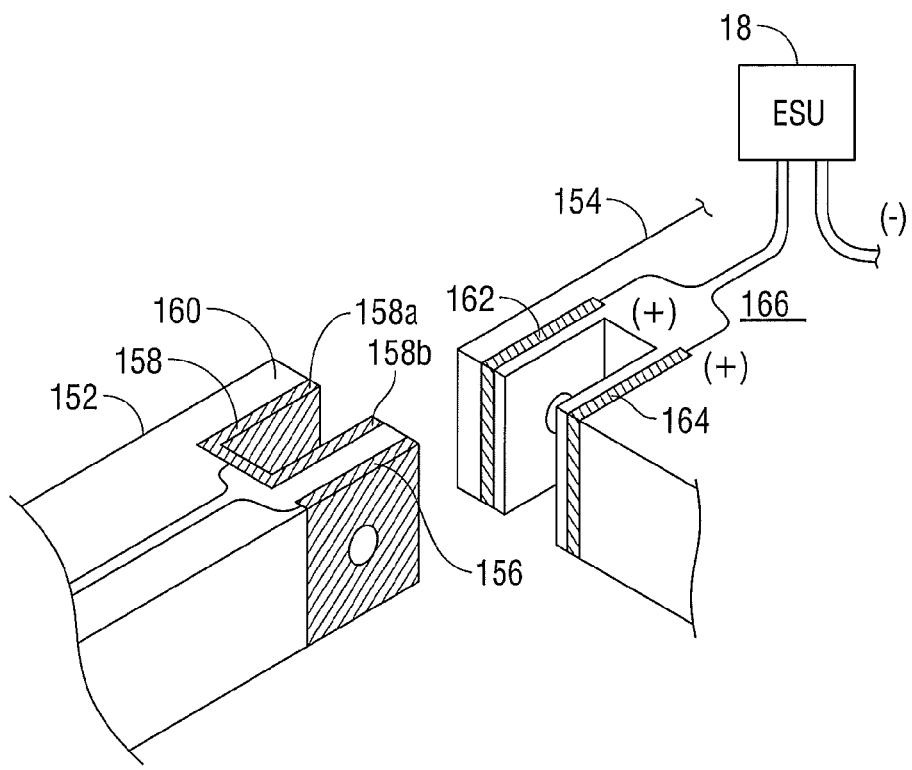
FIG. 5 is a perspective view of an alternate embodiment of modular jaw members configured for capacitive coupling with an elongated shaft wherein multiple plates are employed.

Referring now to FIG. 5, an alternate embodiment of a modular jaw member 152 is configured for capacitive coupling to a base shaft 154. The modular jaw member 154 includes an electrically conductive plate 156 and an electrically conductive U-shaped portion 158 having a pair of generally flat legs or plates 158a and 158b. The conductive plate 156 and U-shaped portion 158 are disposed in an insulative structural body portion 160, and may be electrically coupled to an electrode (not shown) configured to deliver electrosurgical energy to tissue. The base shaft 154 includes first and second conductive plates 162, 164 each electrically coupled to an active terminal (+) of electrosurgical generator 18. The conductive plates 162, 164 are disposed in an insulative body portion 166.

The modular jaw member 152 may be assembled to the base shaft 154 such that the U-shaped portion 158 of jaw member 152 straddles the first conductive plate 162 of the shaft 164. In the assembled configuration, the first conductive plate 162 of the shaft 154 forms a parallel plate capacitor with each of the legs 158a, 158b of the U-shaped portion 158. Additionally, the second conductive plate 164 of the shaft 154 forms a parallel plate capacitor with conductive plate 156 of the modular jaw member 152.

A similar construction may be defined for an opposing jaw member (not shown) configured for capacitive coupling to a return terminal (−), of the generator 18. Since each of the terminals (+), (−) of the generator 18 are capacitively coupled a respective jaw member, e.g., jaw member 152, through plates, e.g., 156, 158a, 158b, 162, 164 forming multiple capacitors, a greater current may be induced through tissue.

Figure 6:
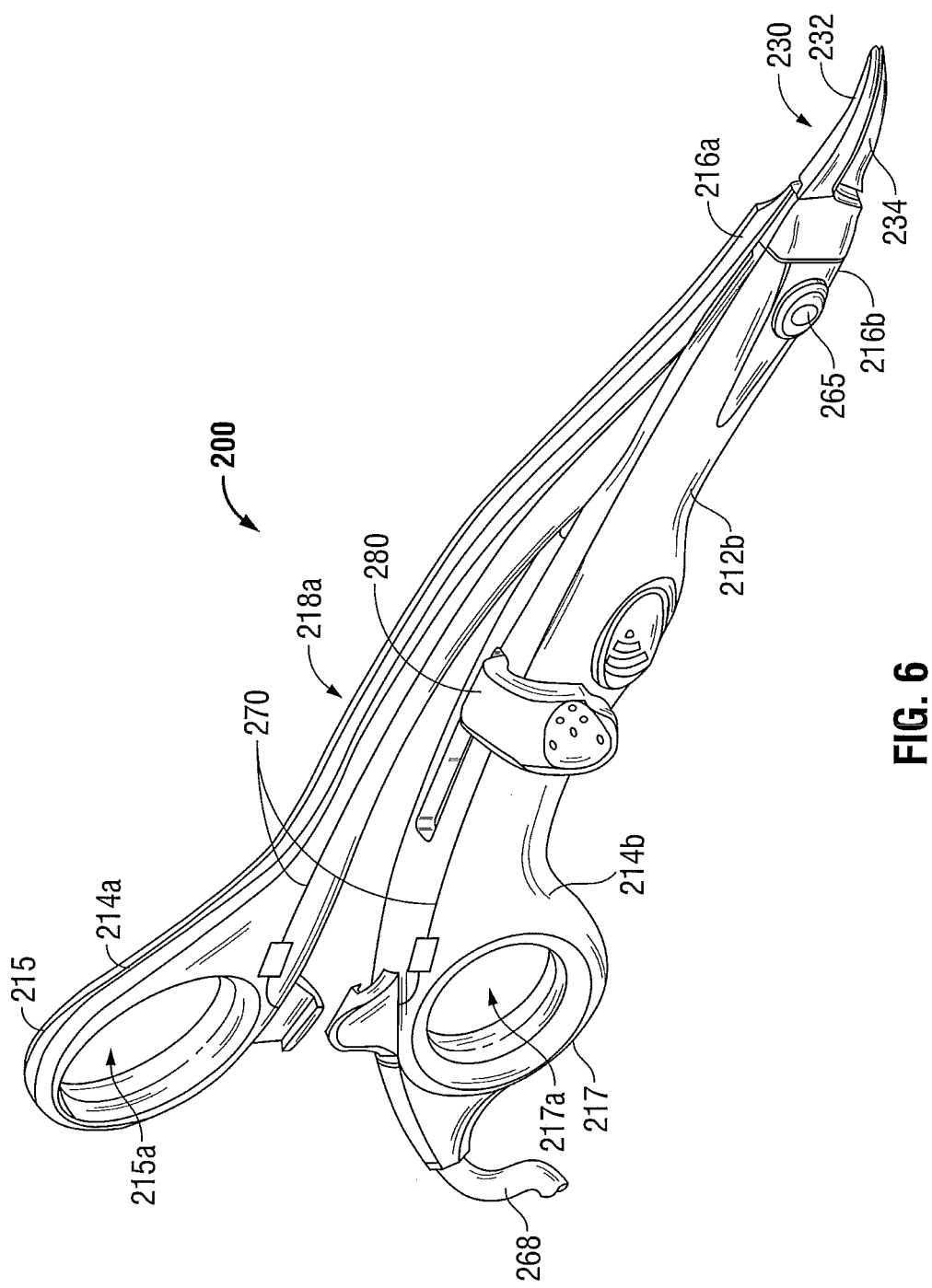
FIG. 6 is an alternate embodiment of a surgical instrument in accordance with the present disclosure configured for use in open surgical procedures.

With regard to FIG. 6, a forceps 200 configured for use in various open surgical procedures may also incorporate many of the features described above. Forceps 200 includes a pair of opposing elongated shafts 212a and 212b having an end effector assembly 230 attached to the distal ends 216a and 216b thereof, respectively. End effector assembly 230 is similar in design to end effector assembly 14 described above with reference to FIG. 1. End effector assembly 230 includes pair of opposing jaw members 232 and 234 that are pivotably connected about a pivot pin 265, and which are movable relative to one another to grasp tissue.

Each shaft 212a and 212b includes a handle 215 and 217, respectively, disposed at the proximal end 214a and 214b thereof which each define a finger hole 215a and 217a, respectively, therethrough for receiving a finger of the clinician. Finger holes 215a and 217a facilitate movement of the shafts 212a and 212b relative to one another which, in turn, pivot the jaw members 232 and 234 from an open position wherein the jaw members 232 and 234 are disposed in spaced relation relative to one another to a clamping or closed position wherein the jaw members 232 and 234 cooperate to grasp tissue therebetween.

An electrosurgical cable 268 couples the instrument 200 to a source of electrosurgical energy, and conductive pathways 270 are provided to transmit electrosurgical energy to the jaw members 232, 234. A knife trigger 280 is provided to induce a knife (not shown) to transect tissue captured between the jaw members 232, 234.

The jaw members 232 and 234 may be configured as modular and selectively removable components separable from the rest of the forceps 200. The jaw members may be coupled with a contactless electrical interface as described above to connect the jaw members 232, 234 to the conductive pathways 270. For example, an inductive coupling as described above with reference to FIGS. 2 and 3 may be provided, or a capacitive coupling interface as described above with reference to FIGS. 4A and 4B may be selected.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a reusable base component, the base component including a handle assembly;
   an electrically-activated modular component removably coupled to the base component, the modular component including an end effector operable from the handle assembly to treat tissue, the end effector responsive to manipulation of the handle assembly to move between first and second configurations;
   a first energy storage component disposed onboard the base component, the first energy storage component electrically coupled to a source of electricity, the first energy storage component includes a first capacitor having a pair of conductive plates separated by a dielectric material; and a second energy storage component onboard the modular component, the second energy storage component electrically insulated from the first energy storage component and arranged with respect to the first energy storage component such that a current may be selectively induced in the modular component by delivery of electrical energy to the first energy storage component, the second energy storage device includes a second capacitor having a pair of conductive plates arranged on opposite sides of the first capacitor, each of the conductive plates of the second capacitor separated from a conductive plate of the first capacitor by a dielectric material, each of the conductive plates of the second capacitor arranged on a respective opposing jaw member.

2. A surgical instrument, comprising:

a reusable base component, the base component including a handle assembly and an elongated tube extending distally therefrom;

an electrically-activated modular component removably coupled to the base component, the modular component including a pair of jaw members operable from the handle assembly and configured to move between an open configuration wherein the jaw members are substantially spaced for receiving tissue and a closed configuration wherein the jaw members are closer together for clamping tissue therebetween;

a first capacitor plate operatively associated with the elongated tube; and a second capacitor plate operatively associated with one of the jaw members, the second capacitor plate forming a capacitor with the first capacitor plate to capacitively couple the base component and the modular component, wherein a pair of additional capacitor plates is operatively associated with the elongated tube, and wherein each of the jaw members includes a capacitor plate disposed thereon forming a respective capacitor with a respective capacitor plate of the elongated tube.

3. The surgical instrument according to claim 2, wherein the first capacitor plate is electrically coupled to a source of electrosurgical energy, and wherein the second capacitor plate is electrically coupled to an electrode configured to deliver the electrosurgical energy to tissue.

4. The surgical instrument according to claim 2, wherein the one of the jaw members includes a pair of additional capacitor plates disposed thereon straddling the first capacitor plate.

5. The surgical instrument according to claim 4, wherein the pair of additional capacitor plates of the one of the jaw members define legs of a generally U-shaped conductive portion of the first jaw member.

6. A surgical instrument, comprising:

a reusable base component, the base component including a handle assembly and an elongated tube extending distally therefrom;

an electrically-activated modular component removably coupled to the base component, the modular component including a pair of jaw members operable from the handle assembly and configured to move between an open configuration wherein the jaw members are substantially spaced for receiving tissue and a closed configuration wherein the jaw members are closer together for clamping tissue therebetween;

a first capacitor plate operatively associated with the elongated tube; and a second capacitor plate operatively associated with one of the jaw members, the second capacitor plate forming a capacitor with the first capacitor plate to capacitively couple the base component and the modular component, wherein the one of the jaw members includes a pair of additional capacitor plates disposed thereon straddling the first capacitor plate.

* * * * *